US00PP17294P2

(12) United States Plant Patent
Hansen

(10) Patent No.: US PP17,294 P2
(45) Date of Patent: Dec. 19, 2006

(54) ***HOSTA* PLANT NAMED 'LONESOME DOVE'**

(50) Latin Name: *Hosta hybrida*
Varietal Denomination: Lonesome Dove

(75) Inventor: Hans Andrew Hansen, Waseca, MN (US)

(73) Assignee: Shady Oaks Nursery , LLC, Waseca, MN (US); part interest ( * ) Notice: Subject to any disclaimer, the term of this patent is extended or adjusted under 35 U.S.C. 154(b) by 0 days.

(21) Appl. No.: 11/244,609

(22) Filed: Oct. 6, 2005

(51) Int. Cl.
*A01H 5/00* (2006.01)

(52) U.S. Cl. ..... Plt./353

(58) Field of Classification Search ..... Plt./353
See application file for complete search history.

*Primary Examiner*—Wendy Haas
(74) *Attorney, Agent, or Firm*—Penny J. Aguirre

(57) ABSTRACT

A new cultivar of *Hosta* named 'Lonesome Dove', that is characterized by its variegated foliage with glaucous green margins comprising about two thirds of the leaf area and creamy white centers that are primarily ovate in shape with additional areas radiating from the base of the leaf. An intermediate lighter green area occurs between the boundaries of the margins and centers and also radiating out from the leaf base. 'Lonesome Dove' is a medium sized *Hosta* with an upright mounded plant habit that blooms in mid summer with lavender flowers that that are held above the foliage on erect scapes.

2 Drawing Sheets

Botanical classification: *Hosta hybrida.*
Cultivar designation: 'Lonesome Dove'.

BACKGROUND OF THE INVENTION

The present invention, *Hosta* 'Lonesome Dove', relates to a new and distinct cultivar of *Hosta,* botanically known as a *Hosta hybrida,* hereinafter referred to as 'Lonesome Dove'.

'Lonesome Dove' originated from a controlled cross, designated 97-243, made by the inventor in Waseca, Minn. in 1997. The pod parent was an unnamed seedling of the inventor's, designated 96-17 (*Hosta* 'Splish Splash'×*H.* 'Sagae') and the pollen parent was *Hosta* 'Blue Moon' (not patented). Neither parent is patented.

Asexual reproduction of the new cultivar was first accomplished by the inventor by division in Waseca, Minn. in 2003. Asexual reproduction of the new cultivar by division and tissue culture has shown that the unique features of 'Lonesome Dove' are stable and reproduced true to type in successive generations.

SUMMARY OF THE INVENTION

The following traits have been repeatedly observed in trials in Minnesota for a period of seven years and represent the characteristics of the new cultivar. These attributes in combination distinguish 'Lonesome Dove' as a new and unique cultivar of *Hosta.*

1. The foliage of 'Lonesome Dove' is variegated with glaucous green margins that comprise about two thirds of the leaf area and creamy white centers. The center variegation is primarily ovate in shape but creamy white areas also radiate from the base of the leaf. An intermediate area of lighter green occurs where the center variegation overlaps the glaucous green margins. The pollen parent, 'Blue Moon', is non-variegated and smaller in size.

2. The leaves of 'Lonesome Dove' have a thick substance, are cupped and broadly ovate in shape.
3. 'Lonesome Dove' is a medium sized *Hosta* with an upright mounded plant habit, reaching a height of about 43 cm (17 inches, exclusive of flower scapes) and a spread of about 81 cm (32 inches).
4. 'Lonesome Dove' blooms in mid summer with lavender flowers that are held above the foliage on erect scapes.

BRIEF DESCRIPTION OF THE DRAWING

The accompanying colored photographs illustrate the overall appearance and distinct characteristics of the new *Hosta* as grown outdoors in Waseca, Minn. for a period of seven years.

The photograph in FIG. 1 was taken in June and provides a view of the foliage and plant habit of 'Lonesome Dove'.

Figure 1:
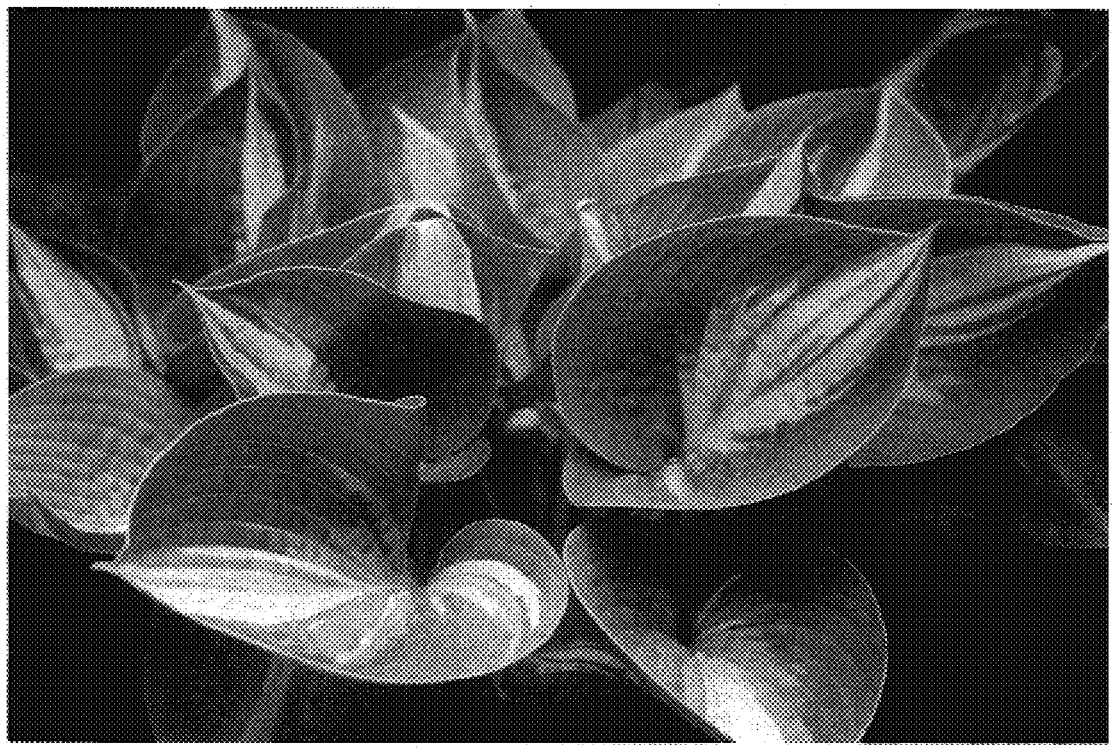
Figure 2:
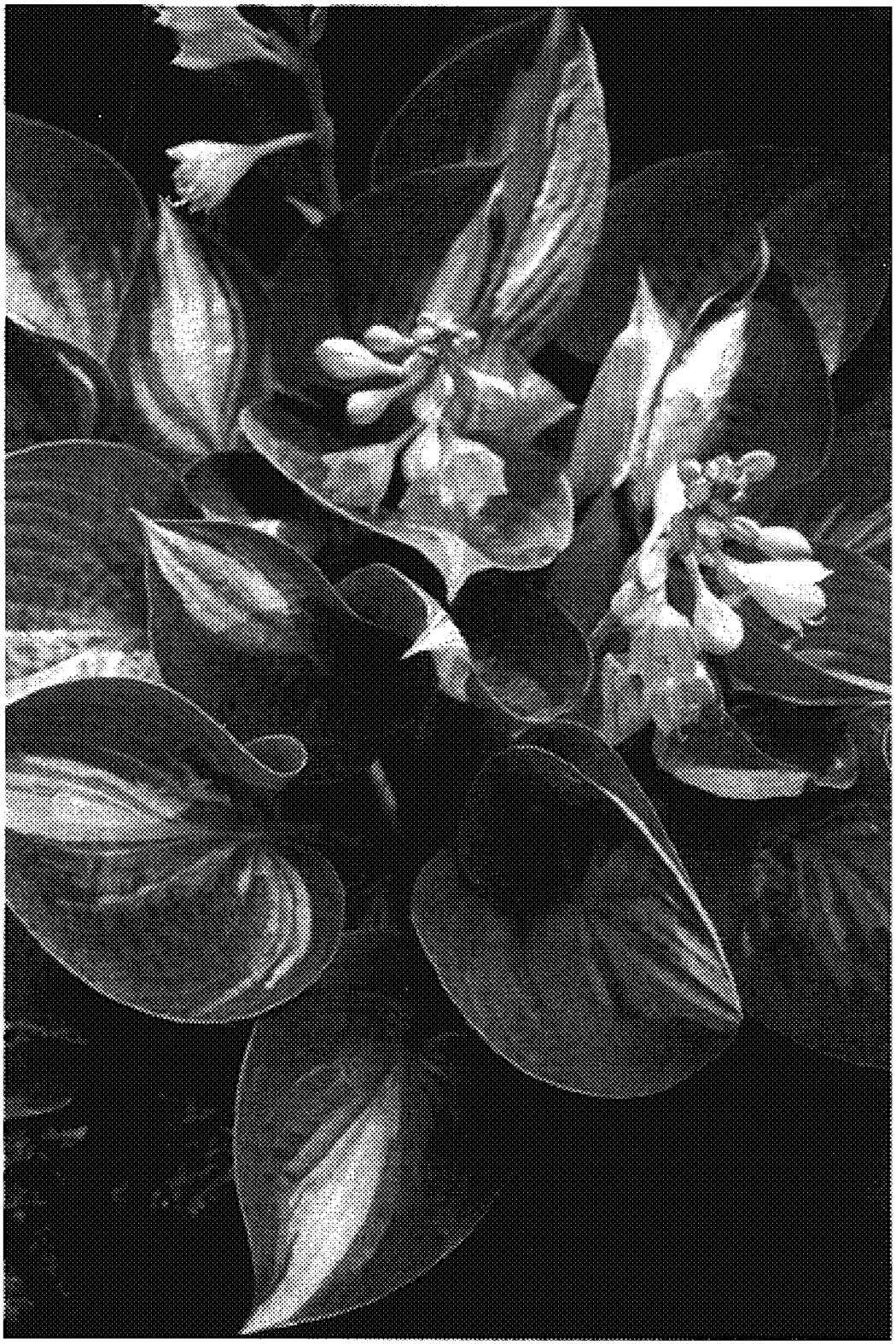

The photograph in FIG. 2 was taken in July and provides a plant 'Lonesome Dove' in bloom.

The colors in the photograph are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of a seven year-old plant of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Lonesome Dove' is a cultivar of *Hosta hybrida.*

Parentage: Pod parent; proprietary seedling No. 96-17 (*H.* 'Splish Splash'×*H.* 'Sagae'), pollen parent; *H.* 'Blue Moon'.

General description:

*Blooming period.*—About July 1 to August 3 in Minnesota.

*Plant habit.*—Herbaceous perennial, clump-forming, upright and mounded habit, medium sized.

*Height and spread.*—Reaches about 43 cm in height (excluding flower scapes) and about 81 cm in width.

*Hardiness.*—U.S.D.A. Zones 3 to 8.

*Culture.*—Light to full shade, moist soils of moderate fertility.

*Diseases and pests.*—No susceptibility or resistance to diseases or other pests has been observed for 'Lonesome Dove'. The thick substance of the leaves may confer some slug resistance.

*Root description.*—Freely branched, fleshy.

*Propagation.*—*In vitro* propagation is the preferred method utilizing typical methods for *Hosta,* division is also possible.

*Root development.*—Rooted transplants from tissue culture fully develop in a 96-cell liner in about 6 to 8 weeks in a greenhouse with average temperatures of about 70° F.

*Growth rate.*—Moderate.

Foliage description:

*Leaf shape.*—Broadly ovate.

*Leaf aspect.*—Cupped.

*Leaf division.*—Simple.

*Leaf base.*—Cordate.

*Leaf apex.*—Cuspidate.

*Leaf venation.*—About 10 to 11 pairs of veins, campylodrome pattern, impressed on upper surface and raised on lower surface, upper surface color matches foliage coloration but slightly lighter on margins, lower surface color matches foliage coloration.

*Leaf margins.*—Entire, flat without undulations.

*Leaf attachment.*—Petiolate.

*Leaf arrangement.*—Basal, radiate spirally from base.

*Leaf surface.*—Glaucous on upper and lower surface.

*Leaf substance.*—Above average.

*Leaf orientation.*—Held at about a 45° angle upright to petiole.

*Leaf variegation pattern.*—Margins comprise about two thirds of the leaf area, the centers are primarily ovate in shape with additional narrower areas radiating from the base of the leaf, an intermediate area exists between the boundaries of the margins and centers and radiating out from the leaf base.

*Leaf color.*—Spring and summer foliage, upper surface; centers 11C to 11D, margins 137B, intermediate area 144A, lower surface; centers 155D, margins 137C, intermediate areas 144B.

*Leaf size.*—Mature leaves; average of 15 cm in length and 11.5 cm in width.

*Leaf quantity.*—About 5 to 7 per shoot (eye).

*Petiole size.*—About 35 cm in length, up to about 1.8 cm in width at leaf blade attachment, average of 1 cm in width.

*Petiole color.*—Variegation radiates into leaf blade, inner surface 144B with edges of 144A, outer surface 155D with edges of 144A.

*Petiole surface.*—Glabrous.

*Petiole shape.*—Sulcate.

Flower scape description:

*Scape shape.*—Round, solid.

*Scape number.*—One per mature eye under normal growing conditions.

*Scape posture.*—Straight, held nearly upright at about 80° to 90° from horizontal.

*Scape size.*—Up to 60 cm in length, average of 5 mm in width.

*Scape color.*—148C.

*Scape surface.*—Glaucous.

*Leaf bracts.*—Not present.

Flower description:

*Inflorescence type.*—Terminal racemes of single tubular-shaped flowers on elongated scapes.

*Lastingness of inflorescence.*—About 3 weeks from first opening bloom to fading of last opening bloom, individual blooms last about one day.

*Flower shape.*—Tubular.

*Flower number.*—About 20.

*Flower fragrance.*—None detected.

*Flower bud shape.*—Spathulate.

*Flower bud size.*—Up to about 4 cm in length and 2 cm in diameter.

*Flower bud color.*—85C.

*Flower size.*—About 6 cm in length and 3 cm in diameter.

*Flower color.*—85 D with inner markings of 85C.

*Pedicels.*—About 4 mm in length, 2 mm in diameter, 85C in color.

*Perianth features.*—Comprised of 6 tepals, 3 interior and 3 exterior, overlapping in expanded region and fused in tube region.

*Tepal shape.*—Oblanceolate.

*Tepal size.*—About 6 cm in length, about 1.3 cm in width.

*Tepal color.*—Outer and inner surface 85D with stripe on inner surface of 85C.

*Tepal texture.*—Glabrous.

*Floral bracts.*—1 per flower, ovate in shape, glabrous surface, 148C blushed with 85C in color, about 2 cm in length and 7 mm in width.

Reproductive organs:

*Gynoecium.*—1 Pistil, style is about 6.5 cm in length, 1 mm in width and 155B in color, stigma is 3-lobed and 155B in color, ovary is superior, compound, composed of 3 locules, 144D in color.

*Androecium.*—6 stamens, filament is 155B in color, 6 cm in length, 1 mm in width, length about same length as perianth, anthers are 3 mm in length, 1.7 mm in width, attachment is versatile, 202A in color, dehiscence is longitudinal, pollen is abundant and 13A in color.

*Fruit.*—Seed pod development has not been observed under the conditions tested.

I claim:

1. A new and distinct cultivar of *Hosta* plant named 'Lonesome Dove' as herein illustrated and described.

* * * * *